United States Patent [19]
Prencipe et al.

[11] Patent Number: 6,110,446
[45] Date of Patent: Aug. 29, 2000

[54] DUAL COMPONENT ANTIPLAQUE AND TOOTH WHITENING COMPOSITION

[75] Inventors: Michael Prencipe, Princeton Junction; Vincent O. Drago, Sayreville; Mike Wong, North Brunswick, all of N.J.; Barry D. Self, Baton Rouge, La.; Malcolm Williams, Piscataway; John Afflitto, Brookside, both of N.J.

[73] Assignee: Colgate Palmolive Company, New York, N.Y.

[21] Appl. No.: 09/166,025

[22] Filed: Oct. 5, 1998

[51] Int. Cl.$^7$ .................. A61K 7/16; A61K 7/20
[52] U.S. Cl. ................................ 424/53; 424/49
[58] Field of Search ......................... 424/49–58

[56] References Cited

U.S. PATENT DOCUMENTS

| | | | |
|---|---|---|---|
| 5,055,209 | 10/1991 | Bridges et al. | 252/8.51 |
| 5,122,365 | 6/1992 | Murayama | 424/53 |
| 5,256,402 | 10/1993 | Prencipe et al. | 424/53 |
| 5,279,816 | 1/1994 | Church et al. | 424/53 |
| 5,302,375 | 4/1994 | Viscio | 424/53 |
| 5,372,802 | 12/1994 | Barrows et al. | 424/53 |
| 5,401,495 | 3/1995 | Murayama | 424/53 |
| 5,424,060 | 6/1995 | Hauschild | 424/53 |
| 5,571,501 | 11/1996 | Toy | 424/49 |
| 5,578,293 | 11/1996 | Prencipe et al. | 424/49 |
| 5,601,803 | 2/1997 | Masters et al. | 424/49 |
| 5,614,174 | 3/1997 | Hsu et al. | 424/49 |
| 5,616,313 | 4/1997 | Williams et al. | 424/53 |
| 5,632,972 | 5/1997 | Williams et al. | 424/53 |
| 5,648,064 | 7/1997 | Gaffar et al. | 424/53 |
| 5,683,680 | 11/1997 | Santalucia et al. | 424/53 |
| 5,690,911 | 11/1997 | Mirajkar et al. | 424/49 |
| 5,690,913 | 11/1997 | Hsu et al. | 424/53 |
| 5,693,314 | 12/1997 | Campbell et al. | 424/49 |
| 5,698,182 | 12/1997 | Prencipe et al. | 424/53 |
| 5,718,886 | 2/1998 | Pellico | 424/53 |
| 5,730,959 | 3/1998 | Prencipe et al. | 424/53 |
| 5,756,073 | 5/1998 | Miller et al. | 424/49 |
| 5,766,574 | 6/1998 | Christina-Beck et al. | 424/53 |
| 5,776,437 | 7/1998 | Burgess et al. | 424/53 |
| 5,785,956 | 7/1998 | Sullivan et al. | 424/52 |
| 5,800,803 | 9/1998 | Mirajkar et al. | 424/49 |
| 5,820,852 | 10/1998 | Burgess et al. | 424/53 |
| 5,820,853 | 10/1998 | Glandorf | 424/52 |
| 5,820,854 | 10/1998 | Glandorf | 424/53 |
| 5,843,406 | 12/1998 | Mordarski et al. | 424/49 |
| 5,846,570 | 12/1998 | Barrow et al. | 424/53 |
| 5,849,269 | 12/1998 | Burgess et al. | 424/53 |
| 5,853,704 | 12/1998 | Zhang et al. | 424/52 |
| 5,885,553 | 3/1999 | Michael | 424/53 |
| 5,885,555 | 3/1999 | Sheehan | 424/53 |
| 5,939,052 | 8/1999 | White et al. | 424/52 |

FOREIGN PATENT DOCUMENTS

| | | | |
|---|---|---|---|
| 0202359 | 11/1986 | European Pat. Off. | A61K 7/20 |
| 2117240 | 3/1983 | United Kingdom | A61K 7/20 |
| 9721419 | 6/1997 | WIPO | A61K 7/20 |
| 9822079 | 5/1998 | WIPO | A61K 7/16 |
| 9917734 | 4/1999 | WIPO | A61K 7/20 |

*Primary Examiner*—Shep K. Rose
*Attorney, Agent, or Firm*—Paul Shapiro

[57] ABSTRACT

A dual component antiplaque and whitening dentifrice composition in which the first component is a paste composition containing an antibacterial agent such as Triclosan and the second component contains a peroxide compound such as hydrogen peroxide in a vehicle thickened with a combination of an inorganic thickeners and an organic thickener other than an alkylene oxide polymer wherein the antiplaque and whitening efficacy of the components is unimpaired when the components are physically separated prior to use and thereafter are mixed upon application to dental tissue.

12 Claims, No Drawings

DUAL COMPONENT ANTIPLAQUE AND TOOTH WHITENING COMPOSITION

BACKGROUND OF THE INVENTION

1. Field of the Invention

The present invention relates to a dual component oral care composition which is effective in the prevention of bacterial plaque accumulation on the teeth as well as in effecting heightened whitening thereof.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of nonionic antibacterial agents have been suggested in the art to retard plaque formation and the oral infections and dental disease associated with plaque formation. For example, halogenated hydroxydiphenyl ether compounds such as Triclosan are well known to the art for their antibacterial activity and have been used in oral compositions to counter plaque formation by bacterial accumulation in the oral cavity.

Many substances such as tea and coffee that a person confronts or comes in contact with on a daily basis can "stain" or reduce the "whiteness" of one's teeth. Consumers consider clean, white teeth to be aesthetically desirable. Dull-looking, stained teeth are objectionable to most people both on the basis of cosmetic appearance and also socially as an indication of poor oral hygiene. Dental gels containing active oxygen liberating ingredients such as hydrogen peroxide, urea peroxide, percarbonates and perborates of alkali and alkaline earth metals have been disclosed in the prior art for whitening teeth. For example, U.S. Pat. No. 5,766,574 discloses a dual component dental whitening composition which comprises a first gel component containing a peroxide compound and a second paste component containing an abrasive such as silica which is incompatible with the peroxide, the first and second dentifrice components being maintained separate from the other until dispensed and combined for application to teeth requiring whitening.

Although the composition disclosed in U.S. Pat. No. 5,766,574 is effective for whitening, when a noncationic antiplaque agent such as Triclosan was included in the abrasive dentifrice component, it was discovered that when the gel and paste components were combined for application to the teeth, the bioavailability of the Triclosan was inhibited to a level whereby little antiplaque benefit was achieved. Investigation of this problem led to the discovery that polyethylene oxide/polypropylene oxide block copolymers conventionally used as a thickening agents in the preparation of peroxide gels were the factor responsible for the impairment of the antiplaque efficacy of the Triclosan.

Thus, there is a clear need in the art to formulate a dental product capable of delivering both an antiplaque agent such as Triclosan and a peroxide whitening agent during tooth brushing whereby the ingredients used to prepare the dentifrice composition do not inhibit the bioavailability of the antiplaque agent so that optimum antiplaque and whitening benefits result.

SUMMARY OF THE INVENTION

In accordance with the present invention there is provided a composition and method for applying a dental composition containing both a nonionic antibacterial agent and a peroxide whitening compound to the teeth, wherein the antibacterial agent and peroxide compound are each incorporated in separate dentifrice components which are physically separated until dispensed for use, the first component being an aqueous composition containing the nonionic antibacterial agent and the second component being a composition containing a peroxide whitening compound in a vehicle thickened with a combination of a inorganic thickener and an organic thickener other than an alkylene oxide polymer, such as a polyethylene oxide/polypropylene oxide block copolymer, whereby unimpaired antiplaque and whitening benefits are achieved upon mixing of the components on application to the teeth.

DESCRIPTION OF THE PREFERRED EMBODIMENTS

The nonionic antibacterial agent used to prepare the first component of the dental composition in accordance with the practice of the present invention is preferably a halogenated diphenyl ether compound. Halogenated diphenyl ether antibacterial compounds desirable from considerations of antiplaque effectiveness and safety include 2,4,4'-trichloro-2'-hydroxydiphenyl ether (Triclosan) and 2,2'-dihydroxy-5,5'-dibromodiphenyl ether. Other useful nonionic antibacterial agents include phenoic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference. The antibacterial agent is incorporated in the first component of the composition of the present invention at concentration of about 0.05 to about 3.0% by weight and preferably about 0.1 to about 1% by weight.

In the practice of the present invention the whitening component containing the peroxide ingredient is formulated as a gel using a vehicle containing the peroxide compound whitening agent in a water/humectant vehicle containing a thickening agent combination of an inorganic thickening agent and an organic thickening compound other than an alkylene oxide polymer.

Examples of suitable peroxide compounds used to prepare the whitening component of the present invention include metal ion free peroxide ingredients such as hydrogen peroxide and organic peroxides such as urea peroxide, glyceryl peroxide and benzoyl peroxide as well as metal ion containing peroxides such as calcium peroxide, and sodium percarbonate. A preferred peroxide compound is hydrogen peroxide.

Typically, the peroxide compound is employed in the composition of the present invention in amounts so that at least about 0.1% by weight of the whitening component comprises a peroxide. Preferably, the peroxide compound comprises from about 1 to about 3% by weight of the whitening component.

Glycerin and polyethylene glycol in combination with water are useful in formulating the vehicle for the peroxide gel whitening component of the present invention. Glycerin and polyethylene glycol are included in the peroxide gel component of the present invention in an amount of from about 2 to about 80% by weight and preferably about 10 to about 50% by weight. Water is incorporated in the gel component of the present invention at a concentration of about 5 to about 90% by weight of the composition and preferably about 15 to about 50% by weight.

The thickening agent used for the formulation of the peroxide gel whitening component which is compatible with nonionic antibacterial agents is a combination of an inorganic thickener and an organic thickener other than an alkylene oxide polymer. The thickening agent combination is present in the peroxide gel component in an amount within the range of about 1 to about 20% by weight and preferably about 3 to 10% by weight.

Examples of inorganic thickeners include fumed silicas such as those available from Cabot & Degussa Corporation under the trademark Cab-o-Sil and Aerosil, Clays such as Laponite and amorphous silicas available from the Huber Company under the trademark Zeodent 115. The inorganic thickener may be incorporated in the peroxide gel at a concentration of from 0.1% to 20% by weight, and preferably from 1% to 6% by weight.

Examples of organic thickeners which may be used in the preparation of the peroxide gel in combination with the inorganic thickener include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose, and carboxyvinyl polymers, commercially available under the trademarks "Carbopol 934, 940, 974 P" from B.F. Goodrich, these polymers consisting of colloidally water soluble polymers of polyacrylic acid cross-linked with from about 0.75% to about 2% of polyallyl sucrose or polyallyl pentaerythritol as a crosslinking agent, often with molecular weights of 4 to 5 million or more. The organic thickener may be incorporated in the antiplaque component peroxide gel of the present invention at a concentration of about 0.1 to about 5% by weight and preferably about 0.5 to about 2.0% by weight.

The peroxide gel component may be prepared by suspending the peroxide in a vehicle thickened with a combination of inorganic and organic thickeners by mixing in any suitable mixing device.

It is critical to the practice of the present invention that a combination of inorganic and organic thickeners be used in the preparation of the peroxide gel component. If organic thickeners alone are used in the formulation of the peroxide gel, such as xanthan and/or Carbopol, the rheology of the gel is not sufficiently like a toothpaste and lacks the stand-up qualities usually associated with dentifrices.

If inorganic thickeners alone are used, such as fumed silica, the gel tends to stiffen considerably on aging, resulting in a gel product that will have a rheology which is in a state of flux and will not be extruded from a dual chamber package in amounts of equal proportion to the paste product. If a clay such as Laponite alone is used, the product will not be stable to peroxide ingredients.

The paste component in which the nonionic antibacterial agent is included is generally prepared using a vehicle which contains water, humectant, abrasive, surfactant and thickener ingredients.

The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 80% by weight and preferably about 40 to about 50% by weight. The water content is in the range of about 10 to about 80% by weight, and preferably from 20% to 50%.

Thickeners which may be used in the preparation of the antibacterial paste component include thickening silicas, such as amorphous silica available from J. M. Huber Company under the trademark Zeodent 115, natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The thickener may be incorporated in the antibacterial paste component of the present invention at a concentration of about 0.1 to about 3% by weight and preferably about 0.5 to about 1% by weight.

Surfactants are incorporated in the antiplaque antibacterial paste component to provide foaming properties. The surfactant is preferably anionic. Suitable examples of anionic surfactants include higher alkyl sulfates such as potassium or sodium lauryl sulfate which is preferred, higher fatty acid monoglyceride monosulfates, such as the salt of the monosulfated monoglyceride or hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine. The surfactant is generally present in the antiplaque paste component at a concentration of about 0.5 to about 5.0% by weight of the component.

Abrasives which may be incorporated in the antiplaque paste component include siliceous materials, such as silica and alumina. A preferred silica is a precipitated amorphous hydrated silica, such as Sorbosil AC-35, marketed by Crossfield Chemicals, or Zeodent 165 from Huber Company. Alumina abrasives include alumina trihydrate, aluminum silicate, calcined alumina and bentonite. The concentration of abrasive in the antiplaque paste component of the present invention will normally be in the range of 15 to about 50% by weight and preferably 20 to 40% by weight.

Fluoride ion-providing salts having anti-caries efficacy may also be incorporated in the paste component of the present invention and are characterized by their ability to release fluoride ions in water and include sodium fluoride, potassium fluoride, a tin fluoride such as stannous fluoride, sodium fluorosilicate, ammonium fluorosilicate and sodium monofluorophosphate. It is preferable to employ a fluoride salt to release about 10–1500 ppm of fluoride ion.

Synthetic anionic polycarboxylates may optionally be included in the antiplaque paste component. Anionic polycarboxylates are well known, being often employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to 1,000,000. These copolymers are available for example as Gantrez AN 139 (M.W. 500,000), AN 119 (M.W. 250,000) and preferably S-97 Pharmaceutical Grade of GAF Corporation. Other operative polymeric polycarboxylates include those disclosed in U.S. Pat. No. 3,956,480, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates include those disclosed in U.S. Pat. Nos. 4,138,477, and 4,183,914, such as copolymers of maleic anhydride with styrene, isobutylene or ethyl vinyl ether, polyacrylic, polyitaconic and polymaleic acids, and sulfoacrylic oligomers of molecular weight as low as 1,000, available as Uniroyal ND-2.

Agents effective against dental calculus such as pyrophosphate salts including the mono, di, tri and tetra alkali metal and ammonium pyrophosphate and tripolyphosphate salts is still another additional ingredient which may be present in the antiplaque paste component of the present invention. Such agents are used in amounts sufficient to reduce calculus and are preferably in amounts which will release about 1% by weight $P_2O_7$ ion and most preferably at least about 1.3% by weight $P_2O_7$ ion.

Plaque buffers such as calcium lactate, calcium glycerophosphate and stronthium polyacrylates may also be included in the abrasive component. Other optional ingredients include vitamins such as vitamin A, C, E, $B_6$, $B_{12}$, K, plant extracts as well as potassium salts useful in the treatment of dentin hypersensitivity such as potassium citrate, potassium chloride, potassium sulfate, potassium tartrate and potassium nitrate.

Peroxide activators such as manganese coordination complexes such as manganese gluconate may also be incorporated in the antiplaque paste component of the present invention. The activator compound when contacted with the peroxide ingredient of the peroxide gel component activates the peroxide compound and accelerates the release of active oxygen to effect rapid whitening action. Other examples of manganese coordination complexes useful for incorporation in the abrasive dentifrice component as peroxide activators are described in U.S. Pat. No. 5,648,064 which is incorporated herein by reference. The manganese coordination complex compounds are included in the antiplaque paste component at a concentration of about 0.005% to about 3% by weight and preferably about 0.05 to about 1.75% by weight.

Other ingredients which may be incorporated in the components of the present invention include pigments, dyes, flavoring and sweetening materials. A striped dental product is obtained in accordance with the practice of the present invention wherein colorants of contrasting colors are incorporated in each of the components used in the practice of the present invention, the colorants being pharmacologically and physiologically nontoxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentifrice component and are generally food color additives presently certified under the Food Drug & Cosmetic Act for use in food and ingested drugs, including dyes such as FD&C Red #3 (sodium salt of tetraiodofluorescein), FD&C Yellow #5 (sodium salt of 4-p-sulfophenylaxo-B-naphtol-6-monosulfonate), FD&C Green #3 (disodium salt of 4-{[4-(N-ethyl-p-sulfobenzylamino)-phenyl]-4-hydroxy-2-sulfoniumphenyl)-methylene}-[1-(N-ethyl-N-p-sulfobenzyl)-3,5-cyclohexadienimine], FD&C Blue #1 (disodium salt of dibenzyldiethyl-diaminotriphenylcarbinol trisulfonic acid anhydrite), FD&C Blue #2 (sodium salt of disulfonic acid of indigotin) and mixtures thereof in various proportions. The concentration of the dye for the most effective result in the present invention is present in an amount from about 0.0005% to about 2% by weight.

It is preferred that the colorant included in one of the components be a pigment such as $TiO_2$ and that the colorant distributed throughout the body of the other component be a dye and that the dye be of a different color than the colorant included in the first dentifrice component.

Any suitable flavoring or sweetening material may also be incorporated in the components of the present invention. Examples of suitable flavoring constituents are flavoring oils, e.g., oils of spearmint, peppermint, wintergreen, sassafras, clove, sage, eucalyptus, marjoram, cinnamon. Lemon, and orange, and methyl salicylate. Suitable sweetening agents include sucrose, lactose, maltose, sorbitol, xylitol, sodium cyclamate, perillartine, and sodium saccharin. Suitably, flavor and sweetening agents may together comprise from 0.01% to 5% by weight or more of the preparations.

To prepare the antiplaque paste component of the present invention, water, humectant, e.g., sorbitol, thickener and sweetener are dispersed in a conventional mixer until the mixture becomes a homogeneous gel phase. Into the gel phase are added a pigment such as $TiO_2$ and a fluoride anticaries agent such as sodium fluoride.

These ingredients are mixed until a homogeneous phase is obtained. Thereafter the polishing agent, polycarboxylate compound, antibacterial agent, flavor and surfactant ingredients are added and the ingredients mixed at high speed under vacuum of about 20–100 mm Hg. The resultant product is a homogeneous, semi-solid, extrudable paste product.

The dual component oral composition of the present invention is packaged in a suitable dispensing container in which the components are maintained physically separated and from which the separated components may be dispensed synchronously. Such containers are known to the art. An example of such container is a dual compartmented dispensing container having collapsible sidewalls disclosed in U.S. Pat. Nos. 4,487,757 and 4,687,663 wherein the container body is formed from a collapsible plastic web and is provided with a partition within the container body defining separate compartment in which the physically separated components are stored and from which they are dispersed through a suitable dispensing outlet.

The following Examples illustrate the present invention. The individual components described below were prepared by following the procedures described above. The amounts of the various ingredients are by weight unless otherwise indicated. The resultant components were deaerated, packaged in tubes or other containers provided with means for physical separation of the individual dentifrice components.

The following examples further illustrate but do not limit this invention.

EXAMPLE I

A combined dual component composition of the present invention, designated "Composition X", composed of a 1:1 volume mixture of paste component A and gel component B of the present invention in which the gel component B was thickened with a combination of fumed silica and xanthan gum was prepared using the ingredients and the amounts listed in Table I. For purposes of comparison, a comparative dual component composition designated Composition Y, composed of an 1:1 volume of paste component A and gel component C thickened with Pluronic F-127 (a polyethylene oxide/polypropylene oxide block copolymer) was prepared using the ingredients also listed in Table I.

TABLE I

| Ingredients | Dentifrice Component | | |
|---|---|---|---|
| | A | B | C |
| Glycerin | 20.0 | 52.0 | 30.0 |
| Carboxymethyl cellulose | 0.8 | — | — |
| Carrageenan | 0.3 | — | — |
| Xanthan | — | 1.50 | — |
| Pluronic F-127 | — | — | 21.0 |
| Hydrogen Peroxide (35% solution) | — | 5.71 | 5.71 |
| Water | 12.510 | 31.84 | 30.43 |
| NaF | 0.486 | — | — |
| MnGluconate | 0.5 | — | — |
| Saccharin | 0.3 | — | — |
| Sorbitol | 9.00 | — | — |
| Polyethylene glycol 600 | — | 1.50 | 10.00 |
| Gantrez Liquid (S-97) | 30.00 | — | — |
| NaOH (50%) | 2.40 | — | — |
| Abrasive Silica*[1] | 20.00 | — | — |
| Silica Thickener*[2] | 1.00 | — | — |
| Fumed Silica | — | 5.75 | — |
| Flavor | 1.00 | — | — |
| Triclosan | 0.600 | — | — |
| Sodium lauryl sulfate | 1.500 | — | — |
| Phosphoric Acid | — | 0.50 | 1.00 |
| Tetrasodium pyorphosphate | — | 0.50 | — |
| FD&C Blue #1 (1% solution) | — | 0.70 | — |

*[1]Zeodent 165
*[2]Zeodent 115

The antiplaque activity of Composition X and comparative Composition Y was assessed using a saliva flow cell model of the type disclosed in the American Journal of Dentistry, Vol. 3, pages S9–S10 (1990).

In the Flow Cell System, Germanium single-pass trapezoid prisms, 50×20×1 mm (Harrick Scientific Corporation, Ossining, N.Y.), were used as a substrate to grow plaque and for internal reflection infrared analysis of the developed plaque. The plates were cleaned by wiping with a saturated alcoholic-KOH solution followed by washing with a 5% Sparkleen® solution (Fisher Scientific Company, Pittsburgh, Pa.), to prepare plate surfaces having surface energy characteristics similar to those of human tooth enamel. This method was effective in removing all organic materials from plates as assessed by internal reflection infrared spectroscopy. In all instances attenuated total reflectance (ATR) was recorded with a Perkin-Elmer 1725X Fourier-transformed infrared spectrophotometer (Perkin-Elmer, Norwalk, Conn.) incorporating a multiple internal reflectance accessory specific for the instrument.

The flow system was set up in an incubator at 37° C., with the flow cells in a vertical position to minimize the entrapment of air. A peristaltic pump produced a steady flow rate.

For each experiment, saliva, stimulated with parafilm, was collected on ice from one of 3 healthy male adults who had refrained from oral care procedures on the day of sampling. To minimize food residuals, saliva was collected at least 2 hours following food intake. Immediately after sampling, the saliva was diluted two-fold with an artificial saliva buffer, pH 7.4, containing ammonium chloride, calcium chloride, manganese chloride, potassium chloride, potassium di-hydrogen orthophosphate, potassium thiocynate, sodium citrate, sodium hydrogen carbonate, di-sodium hydrogen orthophophate and urea (Shellis 1978). Dilution was done to reduce the viscosity and increase the volume of saliva.

Whole saliva was circulated through the flow system at a rate of 1 ml min$^{-1}$, at which time it was replaced with supplemented saliva which consisted of 35 parts whole saliva, 35 parts saliva buffer, 10 parts 2X Modified Eagle Medium (Life Technologies, Inc.), 10 parts 25 mg ml$^{-1}$ porcine gastric mucin (Sigma Chemical Company, St. Louis, Mo.) and 10 parts tryptic soy broth. Circulation continued for up to 96 hours, with the supplemented-saliva being replaced every 24 hours.

To assess the effects of different test samples on plaque formation, the flow cells were pulsed twice daily with the test samples at a flow rate of 10 ml min$^{-1}$ for a specific time. To evaluate dentifrices in the flow system, slurries were prepared by dissolving dentifrice in water (2:1, weight/weight, dentifrice:water), followed by centrifugation for 10 min at 10000 rpm and 25° C. The resulting supernatants were used in the treatment process. Residuals from test solutions were removed by rinsing the flow cell for 30 min. At the end of the experimental period, the flow cells were rinsed with deionized distilled water for 20 min to remove loosely-bound materials. The flow system was then disassembled and the test plates were air dried in a vertical position prior to analysis.

Between experiments, the flow cell components, connectors and silicone tubing were washed in a 5% Sparkleen® solution, rinsed with deionized distilled water, and then autoclaved for 30 min at 121° C.

After drying overnight, the plates were analyzed by infrared spectroscopy, which provides a semiquantitative assessment of the chemical composition of plaque grown. Scanning was performed at a rate of 0.2 cm s$^{-1}$ and a resolution of 4 cm$^{-1}$. Data management software from Perkin-Elmer was employed to manipulate the spectra.

Plaque Index

A plaque score was calculated, using the FTIR absorption band intensities at 3300, 1650, 1545 and 1080 cm$^{-1}$ from the infrared spectrum as follows:

Plaque Score=$abs_{3300}+abs_{1650}+abs_{1545}+abs_{1080}$ where abs is the maximum absorbance at the various wavenumbers. The wavenumbers selected represent the infrared adsorption by salivary components and bacteria on Ge prisms. The extent of surface coverage is measured since film thickness greater than 1 micron is not amenable to analysis by ATR infrared spectroscopy. The test agents were assessed for overall plaque inhibition versus a control which was simultaneously run in the system. The results are recorded in Table II below. The control was a commercial antiplaque toothpaste containing 0.3% by weight Triclosan, designated "Composition T".

TABLE II

| Composition | Plaque Score |
|---|---|
| X | 0.72 |
| Y | 3.07 |
| T | 1.06 |

The results recorded in Table II show that compared to the commercial toothpaste T, the antiplaque activity of Composition X was not impaired whereas the antiplaque activity of the comparative Composition Y was appreciably inhibited.

EXAMPLE II

The procedure of Example I was repeated except peroxide formulations with combination of xanthan and fumed silica (Component D) were prepared as well as comparative dentifrice formulations containing fumed silica alone (Component E), and xanthan alone (Component F). The ingredients of peroxide Components D, E and F are recorded in Table III below.

TABLE III

| Ingredients | Dentifrice Component | | |
|---|---|---|---|
| | D | E | F |
| Glycerin | 52.0 | 52.0 | 52.0 |
| Xanthan | 1.00 | — | 1.00 |
| $H_2O_2$ (35% solution) | 5.71 | 5.71 | 5.71 |
| PEG 600 | 1.5 | 1.5 | 1.50 |
| Fumed Silica | 5.75 | 5.75 | — |
| Phosphoric Acid | 0.50 | 0.50 | 0.50 |
| Tetrasodium pyrophosphate | 0.50 | 0.50 | 0.50 |
| FD&Q Blue #1 (1% solution) | 0.70 | 0.70 | 0.70 |
| Water - QS to 100% | | | |

The viscosity stability of the peroxide components was measured over a 4 week period at room temperature (22° C.) stored in sealed plastic tubes using Brookfield Viscometer Model RUTD2. Measurements were taken at 5 rpm with spindle E at room temperature. The results are recorded in Table IV below.

TABLE IV

| | Brookfield Viscosity (x 100,000 cps) | | |
|---|---|---|---|
| | 1 Day | 1 Week | 4 Weeks |
| D | 25 | — | 33 |
| E | — | 60 | 100 |

The results recorded in Table IV show that when silica alone is used to prepare the peroxide gel (Component E), the gel progressively thickens over time to unacceptable levels (i.e., a Brookfield Viscosity of up to 1,000,000 cps after 4 weeks at room temperature) whereas very little progressive thickening was observed for the xanthan/fumed silica thickened peroxide gel (Component D). Peroxide gel Component F thickened with xanthan gum alone did not exhibit stand-up, a property lid dentifrice compositions.

EXAMPLE III

Bovine teeth stained with tea and coffee were soaked overnight with Composition X. Thee bovine teeth were measured for their L* values before and after treatment using a Minolta Chromometer. The L* value is a measure of the whiteness of the tooth: the higher the L* value the whiter the teeth. The L* values for the teeth before and after treatment with Composition X are recorded in Table V below.

TABLE V

| Tooth # | L* value before soaking | L* value after soaking |
|---|---|---|
| 1 | 27 | 53 |
| 2 | 29 | 49 |
| 3 | 36 | 58 |
| 4 | 34 | 51 |

The L* value data recorded in Table V shows a significant increase in whiteness after soaking the bovine teeth in Composition X which increase was also readily visible to the naked eye.

EXAMPLE IV

Dentifrice Component A, when tested for aging stability by filling tubes or pumps with Component B, sealing the tubes and exposing the tubes to 120° F. indicated, no gassing or peroxide in stability after 6 weeks of exposure.

What is claimed is:

1. A dual component antiplaque and tooth whitening oral composition in which a first component is a semi-solid abrasive paste which is free of an alkylene oxide polymer and contains a nonionic antibacterial agent and the second component is a semi-solid, abrasive free gel which contains a peroxide compound in a vehicle thickened with a combination of an inorganic thickener compound and an organic thickener compound other than an alkylene oxide polymer, the first and second components being synchronously extrudable when dispensed for application to the teeth, the first and second components being physically segregated prior to use, the components when mixed upon application to teeth providing substantially unimpaired antiplaque and tooth whitening effect.

2. The composition of claim 1 wherein the nonionic antibacterial agent is Triclosan.

3. The composition of claim 1 wherein the organic thickener is selected from natural and synthetic gums and polymers other than alkylene oxide polymers.

4. The composition of claim 3 wherein the organic thickener is xanthan gum.

5. The composition of claim 1 wherein the inorganic thickener is fumed silica.

6. The composition of claim 1 wherein the organic thickener and inorganic thickener are each present in the composition from about 0.1 to about 10% by weight.

7. A method for the simultaneous antiplaque and whitening treatment of teeth which comprises preparing a dual component oral composition in which a first component is a semi-solid abrasive paste which is free of an alkylene oxide polymer and contains an antibacterial agent and a second component is a semi-solid abrasive free gel composition containing a peroxide compound in a vehicle thickened with a combination of an inorganic thickener compound and an organic thickener compound other than an alkylene oxide polymer, maintaining the first component physically separated from a second component, synchronously extruding the first and second components and then mixing the extruded components upon application to the teeth whereby antiplaque and whitening efficacy is substantially unimpaired.

8. The method of claim 7 wherein the nonionic antibacterial agent is Triclosan.

9. The method of claim 7 wherein the organic thickener is selected from natural and synthetic gums and polymers.

10. The method of claim 9 wherein the organic thickener is xanthan gum.

11. The method of claim 7 wherein the inorganic thickener is fumed silica.

12. The method of claim 7 wherein the organic thickener and inorganic thickener are each present in the composition from about 0.1 to about 10% by weight.

* * * * *